United States Patent
Lui et al.

(10) Patent No.: US 8,314,242 B2
(45) Date of Patent: Nov. 20, 2012

(54) PROCESS FOR THE PREPARATION OF 4-AMINOBUT-2-ENOLIDES

(75) Inventors: Norbert Lui, Odenthal (DE); Jens-Dietmar Heinrich, Burscheid (DE)

(73) Assignee: BayerCrop Science AG, Monheim (DE)

(*) Notice: Subject to any disclaimer, the term of this patent is extended or adjusted under 35 U.S.C. 154(b) by 0 days.

(21) Appl. No.: 12/858,031

(22) Filed: Aug. 17, 2010

(65) Prior Publication Data

US 2011/0054182 A1 Mar. 3, 2011

Related U.S. Application Data

(60) Provisional application No. 61/235,878, filed on Aug. 21, 2009.

(30) Foreign Application Priority Data

Aug. 18, 2009 (EP) .................................. 09168068

(51) Int. Cl.
*C07D 405/06* (2006.01)
*C07D 405/02* (2006.01)

(52) U.S. Cl. .................................. 546/284.4

(58) Field of Classification Search .................. None
See application file for complete search history.

(56) References Cited

U.S. PATENT DOCUMENTS

| 5,424,436 | A | * | 6/1995 | Goe et al. ................. | 546/329 |
| 2009/0253749 | A1 | * | 10/2009 | Jeschke et al. ........... | 514/336 |
| 2010/0190990 | A1 | | 7/2010 | Lui et al. | |
| 2010/0204480 | A1 | | 8/2010 | Lui et al. | |

FOREIGN PATENT DOCUMENTS

| EP | 2 039 678 A1 | 3/2009 |
| EP | 2 042 496 A1 | 4/2009 |
| WO | WO 2007/115644 A1 | 10/2007 |
| WO | WO 2007115644 A1 * | 10/2007 |

OTHER PUBLICATIONS

Shandala et al., Reaction of Methyl Tetronate with Some Amines, Synthesis of Substituted 4-Amino-2-enolides, 21 J. Heterocyclic Chem. 1753 (1984).*
Smith & March, March's Advanced Organic Chemistry: Reactions, Mechanisms, and Structure, 5th Ed., Wiley-Interscience Publ'n (2002).*
Michael B. Smith & Jerry March, March's Advanced Organic Chemistry: Reactions, Mechanisms, and Structure, 5th ed. Wiley-Interscience Publication (2001).*
Mavrov, M.V. and Kucherov, V.F., "Nucleophilic reactivity of conjugated bromoallenes," *Dokl. Vses. Konf. Khim. Atsetilena* 1:461-467, Accessed at STN, Accession No. 1973:417999 ZCAPLUS (1973).
Shandala, M.Y., et al., "Reaction of Methyl Tetronate with some Amines. Synthesis of Substituted 4-Aminobut-2-enolides," *J. Heterocyclic Chem.* 21:1753-1754, Journal of Heterocyclic Chemistry, USA (Nov.-Dec. 1984).
English Language Translation of International Search Report for International Application No. PCT/EP2010/004800, European Patent Office, The Netherlands, mailed on Oct. 20, 2010.

* cited by examiner

*Primary Examiner* — Janet Andres
*Assistant Examiner* — Timothy R Rozof
(74) *Attorney, Agent, or Firm* — Sterne, Kessler, Goldstein & Fox P.L.L.C.

(57) ABSTRACT

Process for the preparation of 4-aminobut-2-enolide compounds of the formula (I):

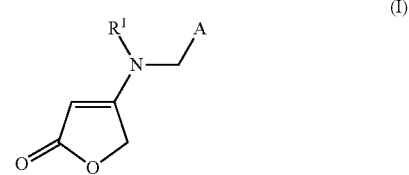

comprising reaction of a 4-(methylamino)furan-2(5H)-one compound of the formula (II)

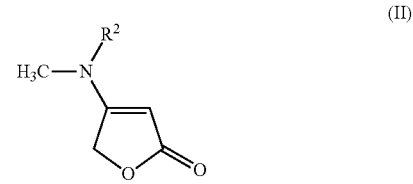

with an amine of the formula (III)

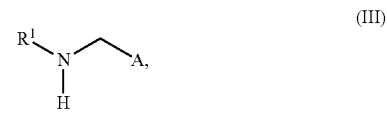

in which $R^1$ and A have the definitions mentioned in the description, optionally in the presence of a Brønstedt acid.

11 Claims, No Drawings

PROCESS FOR THE PREPARATION OF 4-AMINOBUT-2-ENOLIDES

The present invention relates to a process for the preparation of 4-aminobut-2-enolides.

Certain substituted 4-aminobut-2-enolide compounds are disclosed as insecticidal compounds in EP-A-0 539 588 and WO 2007/115644. They can be prepared by various methods.

Thus, for example, Heterocycles Vol. 27, No. 8, pages 1907 to 1923 (1988) and EP-A-0 539 588 state that enaminocarbonyl compounds (3) can be prepared from anhydrous tetronic acid (1) and an amine (2), as shown in Scheme 1. This process is, however, not very suitable for the industrial production of enaminocarbonyl compounds since the anhydrous tetronic acid (1) cannot be economically prepared.

Scheme 1:

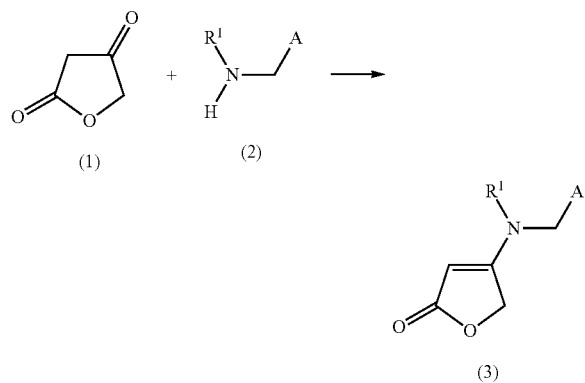

Tetronic acid has not been commercially available to date in large amounts, so that it must be prepared starting from acetoacetic ester via bromination and subsequent hydrogenation (cf. Synthetic Communication, 11(5), pages 385 to 390 (1981)) for use in the process described above. The relatively low yield of tetronic acid (usually less than 40%) and the condition that tetronic acid must be anhydrous give rise to high costs.

A further process for the preparation of tetronic acid is described in Swiss Patent Specification 503 722. 4-chloroacetoacetic ester is reacted with an aromatic amine to give 3-arylaminocrotonolactone, the tetronic acid being liberated after subsequent treatment with mineral acid. The tetronic acid can be isolated only by distillation under a high vacuum, which is disadvantageous for the industrial use of this process.

EP-A-0 153 615 likewise describes a multistage process for the preparation of tetronic acid, which starts from 2,4-dichloroacetoacetic esters and is not very suitable for industrial production. This process requires many complicated stages and gives the desired tetronic acid in a comparatively moderate yield of 65%.

A further process for the preparation of tetronic acid starting from malonic esters and chloroacetyl chloride is disclosed in J. Chem. Soc. Perkin Trans. 1 (1972), 9/10, 1225-1231. This process gives the desired target compound but with a yield of only 43%.

Tetrahedron Letters, No. 31, pages 2683 and 2684 (1974) describes, inter alia, the preparation of tetronic acid, which is reproduced in Scheme 2. The starting material used there is dimethyl acetylenedicarboxylate.

Scheme 2:

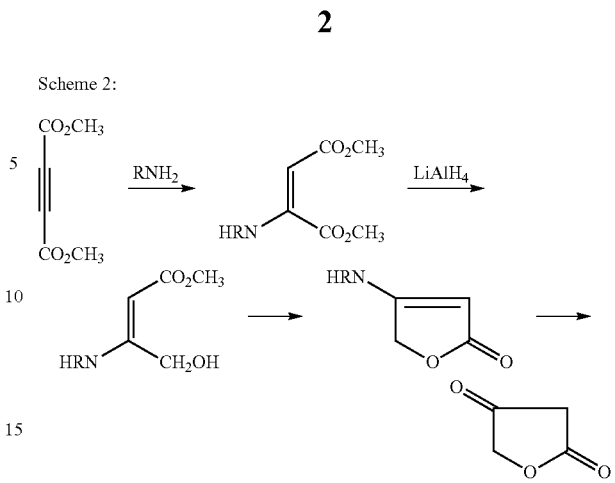

A disadvantage of this process is the low overall yield of only 30% and the use of expensive starting materials, for example lithium aluminium hydride (LiAlH$_4$).

A process for the preparation of 4-amino-2(5H)-furanones substituted on the nitrogen, which starts from tetronic acid, is described in Heterocycles, Vol. 27, No. 8, 1988, 1907-1923. This process starts from a 4-chloroacetoacetic ester, which is reacted with the corresponding amines, the reaction to give the aminofuran being carried out in one step. The amine with glacial acetic acid is added to a solution of 4-chloroacetoacetic ester in benzene and the resulting mixture is refluxed for several hours. The yields of 4-methylamino-2(5H)-furanone in this synthesis are only 40%.

A further process for the preparation of substituted 4-aminobut-2-enolides is described by Mowafak et al. in J. Heterocyclic Chem., 21, 1753-1754 (1984). This process starts from methyl tetronate, the desired compounds being prepared by reaction with amines. The preparation of methyl tetronate takes place via a multistage synthesis in the dry solvent and expensive chemicals, for example, 4-bromo-3-methoxybut-3-enecarboxylic ester, are used, so that the process is not advantageous industrially.

EP-A-0 123 095 discloses a process in which tetronamide is prepared from 3-amino-4-acetoxycrotonic ester. The starting material 3-amino-4-acetoxycrotonic ester is, however, expensive and therefore can be prepared only by an expensive procedure, so that here too this synthesis is unsuitable for industrial production.

WO 2007/115644 describes the preparation of specific 4-aminobut-2-enolides, for example of 4-[[(6-chloropyridin-3-yl)methyl](3,3-dichloroprop-2-en-1-yl)amino]furan-2 (5H)-one by reaction of 4-[[(6-chloropyridin-3-yl)methyl]amino]furan-2(5H)-one with 3-bromo-1,1-dichloroprop-1-ene or by reaction of 4-[((2-fluoroethyl)amino]furan-2(5H)-one with 2-chloro-5-chloromethylpyridine. The reactions are preferably carried out with hydrides of lithium or of sodium. Here too, these substrates are expensive and, for safety reasons, can be handled only with difficulty.

Starting from this prior art, it is therefore the object to provide a process for the preparation of 4-aminobut-2-enolide compounds which can be carried out easily and economically so that the process can also be used for industrial production of 4-aminobut-2-enolide compounds and gives the 4-aminobut-2-enolide compounds with high yield and sufficient purity, so that no complicated purification methods are required.

A process for the preparation of 4-aminobut-2-enolide compounds which avoids the abovementioned disadvantages and which can be carried out easily and economically, in particular because the 4-aminobut-2-enolide compounds according to the invention are obtained with good yields and in high purity so that complicated workup or purification of the direct reaction product is not usually required, has now been found.

The invention therefore relates to the process described below for the preparation of 4-aminobut-2-enolide compounds of the formula (I):

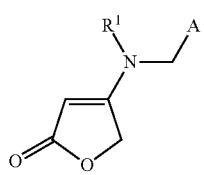
(I)

in which $R^1$ and A represent the Chemical groups defined further below.

The process according to the invention for the preparation of 4-aminobut-2-enolide compounds of the formula (I) comprises the reaction of a 4-(methylamino)furan-2(5H)-one compound of the formula (II)

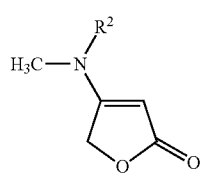
(II)

with an amine of the formula (III)

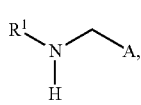
(III)

in which
$R^1$ represents hydrogen, $C_{1-12}$-alkyl, $C_{1-12}$-haloalkyl, $C_{2-12}$-alkenyl, $C_{2-12}$-haloalkenyl, $C_{2-6}$-alkynyl, $C_{3-8}$-cyclo alkyl, $C_{3-8}$-cycloalkyl-$C_{1-6}$-alkyl, $C_{3-8}$-halocyclo alkyl, $C_{1-12}$-alkoxy, $C_{1-6}$-alkoxy-$C_{1-6}$-alkyl, $C_{3-8}$-halocycloalkyl-$C_{1-6}$-alkyl or aryl-$C_{1-6}$-alkyl, preferably $R^1$ represents $C_{1-6}$-alkyl, $C_{1-6}$-haloalkyl, $C_{2-6}$-alkenyl, $C_{2-6}$-haloalkenyl, $C_{2-6}$-alkynyl, $C_{3-8}$-cycloalkyl, $C_{3-8}$-cycloalkyl-$C_{1-6}$-alkyl, $C_{3-8}$-halocycloalkyl, $C_{3-8}$-halocycloalkyl-$C_{1-6}$-alkyl or $C_{1-6}$-alkoxy-$C_{1-6}$-alkyl, particularly preferably methyl, ethyl, propyl, propylene, vinyl, allyl, propargyl, cyclopropyl, $C_{1-6}$-alkoxy-$C_{1-6}$-alkyl, 2-fluoroethyl, 2,2-difluoroethyl or 2-fluorocyclopropyl, very particularly preferably methyl, ethyl, n-propyl, n-prop-2-enyl, n-prop-2-ynyl, cyclopropyl, methoxyethyl, 2-fluoroethyl or 2,2-difluoroethyl;
$R^2$ represents $C_{1-12}$-alkyl, aryl or aryl-$C_{1-6}$-alkyl, preferably $R^2$ represents $C_1$-$C_6$-alkyl, phenyl or aryl-$C_{1-6}$-alkyl, particularly preferably methyl or ethyl; and
A represents pyrid-2-yl, pyrid-4-yl or pyrid-3-yl, which is optionally substituted in the 6-position by F, Cl, Br, $CH_3$, $CF_3$, or $OCF_3$, or represents pyridazin-3-yl which is optionally substituted in the 6-position by Cl or $CH_3$, or represents pyrazin-3-yl, 2-chloropyrazin-5-yl or represents 1,3-thiazol-5-yl optionally substituted in the 2-position by Cl or $CH_3$, or represents pyrimidinyl, pyrazolyl, thiophenyl, oxazolyl, isoxazolyl, 1,2,4-oxadiazolyl, isothiazolyl, 1,2,4-triazolyl or 1,2,5-thiadiazolyl, which is optionally substituted by F, Cl, Br, CN, $NO_2$, $C_{1-4}$-alkyl, $C_{1-3}$-alkylthio or $C_{1-3}$-alkylsulphonyl, where each of the radicals $C_{1-4}$-alkyl, $C_{1-3}$-alkylthio and $C_{1-3}$-alkylsulphonyl may be substituted by F and/or chlorine, or represents a substituted heterocyclyl of the following formula

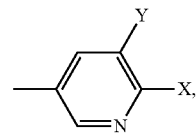

in which
X represents halogen, $C_{1-12}$-alkyl or $C_{1-12}$-haloalkyl and
Y represents halogen, $C_{1-12}$-alkyl, $C_{1-12}$-haloalkyl, $C_{1-12}$-haloalkoxy, azido or CN;
preferably A represents a substituted heterocyclyl selected from 6-fluoropyrid-3-yl, 6-chloropyrid-3-yl, 6-bromopyrid-3-yl, 6-methylpyrid-3-yl, 6-trifluoromethylpyrid-3-yl, 6-trifluoromethoxypyrid-3-yl, 6-chloro-1,4-pyridazin-3-yl, 6-methyl-1,4-pyridazin-3-yl, 2-chloro-1,3-thiazol-5-yl or 2-methyl-1,3-thiazol-5-yl, 2-chloropyrimidin-5-yl, 2-trifluoromethylpyrimidin-5-yl, 5,6-difluoromid-3-yl, 5-chloro-6-fluoropyrid-3-yl, 5-bromo-6-fluoropyrid-3-yl, 5-iodo-6-fluoropyrid-3-yl, 5-fluoro-6-chloropyrid-3-yl, 5,6-dichloropyrid-3-yl, 5-bromo-6-chloropyrid-3-yl, 5-iodo-6-chloropyrrid-3-yl, 5-fluoro-6-bromopyrid-3-yl, 5-chloro-6-bromopyrid-3-yl, 5,6-dibromopyrid-3-yl, 5-fluoro-6-iodopyrid-3-yl, 5-chloro-6-iodoprid-3-yl, 5-bromo-6-iodopyrid-3-yl, 5-methyl-6-fluoropyrid-3-yl, 5-methyl-6-chloropyrid-3-yl, 5-methyl-6-bromopyrid-3-yl, 5-methyl-6-iodopyrid-3-yl, 5-difluoromethyl-6-fluoropyrid-3-yl, 5-difluoromethyl-6-chloropyrid-3-yl, 5-difluoromethyl-6-bromopyrid-3-yl or 5-difluoromethyl-6-iodopyrid-3-yl, particularly preferably A represents a substituted heterocyclyl selected from 6-fluoropyrid-3-yl, 6-chloropyrid-3-yl, 6-bromopyrid-3-yl, 6-chloro-1,4-pyridazin-3-yl, 2-chloro-1,3-thiazol-5-yl, 2-chloropyrimidin-5-yl, 5-fluoro-6-chloropyrid-3-yl, 5,6-dichloropyrid-3-yl, 5-bromo-6-chloropyrid-3-yl, 5-fluoro-6-bromopyrid-3-yl, 5-chloro-6-bromopyrid-3-yl, 5,6-dibromopyrid-3-yl, 5-methyl-6-chloropyrid-3-yl, 5-chloro-6-iodopyrid-3-yl or 5-difluoromethyl-6-chloropyrid-3-yl, very particularly preferably A represents a substituted heterocyclyl selected from 6-chloropyrid-3-yl, 6-bromopyrid-3-yl, 6-chloro-1,4-pyridazin-3-yl, 2-chloro-1,3-thiazol-5-yl, 5-fluoro-6-chloropyrid-3-yl and 5-fluoro-6-bromopyrid-3-yl,
optionally in the presence of a Brønstedt acid.

Surprisingly, it was found that, in the reaction or conversion according to the invention, the exchange of the methylalkylamine radical in the compound of the formula (II) for the amine of the formula (III) takes place in very good yields and that the tetronic acid does not dimerize under the reaction conditions although such a dimerization was to be expected according to J. Chem. Soc. (1947) page 1365.

The reaction according to the invention can furthermore be carried out in the presence of solvents (diluents). The solvent is preferably used in an amount such that the reaction mixture remains readily stirrable during the entire process. Suitable solvents for carrying out the process or reaction according to the invention are all organic solvents which are inert under the reaction conditions. According to the invention, solvents are also understood as meaning mixtures of pure solvents.

Solvents which are suitable according to the invention are in particular halohydrocarbons, such as chlorohydrocarbons (e.g. tetrachloroethylene, tetrachloroethane, dichloropropane, methylene chloride, dichlorobutane, chloroform, carbon tetrachloride, trichloroethane, trichloroethylene, pentachloroethane, difluorobenzene, 1,2-dichloroethane, chlorobenzene, bromobenzene, dichlorobenzene, chlorotoluene, trichlorobenzene), ethers (e.g. ethyl propyl ether, methyl tert-butyl ether, n-butyl ether, anisole, phenetole, cyclohexyl methyl ether, dimethyl ether, diethyl ether, dimethyl glycol diphenyl ether, dipropyl ether, diisopropyl ether, di-n-butyl ether, diisobutyl ether, diisoamyl ether, ethylene glycol dimethyl ether, isopropyl ethyl ether, methyl tert-butyl ether, tetrahydrofuran, methyltetrahydrofuran, dioxane, dichlorodiethyl ether, methyl-THF and polyethers of ethylene oxide and/or of propylene oxide), nitrohydrocarbons (e.g. nitromethane, nitroethane, nitropropane, nitrobenzene, chloronitrobenzene, o-nitrotoluene), nitriles (e.g. acetonitrile, methylnitrile, propionitrile, butyronitrile, isobutyronitrile, benzonitrile, phenylnitrile, m-chlorobenzonitrile) and tetrahydrothiophene dioxide and dimethyl sulphoxide, tetramethylene sulphoxide, dipropyl sulphoxide, benzyl methyl sulphoxide, diisobutyl sulphoxide, dibutyl sulphoxide, diisoamyl sulphoxide; sulphones, such as dimethyl, diethyl, dipropyl, dibutyl, diphenyl, dihexyl, methyl ethyl, ethyl propyl, ethyl isobutyl and pentamethylene sulphone, aliphatic, cycloaliphatic or aromatic hydrocarbons (e.g. pentane, n-hexane, n-heptane, n-octane, nonane, so-called "White Spirits" comprising components having boiling points in the range, for example, from 40° C. to 250° C., cymene, benzene fractions within a boiling range from 70° C. to 190° C., cyclohexane, methylcyclohexane, petroleum ether, naphtha, octane, benzene, toluene, xylene; esters, such as methyl, ethyl, butyl and isobutyl acetate, and dimethyl, dibutyl and ethylene carbonate), amides (e.g. hexamethylenephosphorotriamide, formamide, N,N-dimethylacetamide, N-methylformamide, N,N-dimethylformamide, N,N-dipropylformamide, N,N-dibutylformamide, N-methylpyrrolidine, N-methylcaprolactam, 1,3-dimethyl-3,4,5,6-tetrahydro-2 (1H)pyrimidine, octylpyrrolidone, octylcaprolactam, 1,3-dimethyl-2-imidazolinedione, N-formylpiperidine, N,N'-1, 4-diformylpiperazine), and aliphatic alcohols (e.g. methanol, ethanol, n-propanol and isopropanol and n-butanol) or mixtures thereof.

Dioxane, butyronitrile, propionitrile, acetonitrile, butylacetate, DME, toluene, methyl-THF, dichlorobenzene, chlorobenzene, n-heptane, isobutanol, n-butanol, ethanol, methyl tert-butyl ether, isopropyl ethyl ether and mixtures thereof are preferably used as solvents for the process according to the invention or the reaction.

Depending on the starting compounds used, the process according to the invention or the reaction can be carried out as such, i.e. without addition of solvents.

Suitable Brønstedt acids according to the invention are in principle all organic and inorganic acids. Brønstedt acids preferred according to the invention are phosphoric acid ($H_3PO_4$), sulphuric acid ($H_2SO_4$), hydrochloric acid (HCl), hydrobromic acid (HBr), hydrofluoric acid (HF), potassium hydrogen sulphate ($KHSO_4$), trifluoroacetic acid, acetic acid, methanesulphonic acid and p-toluenesulphonic acid. Phosphoric acid, sulphuric acid, potassium hydrogen sulphate and trifluoroacetic acid are particularly preferred according to the invention.

The Brønstedt acids may be present either in anhydrous or in water-containing form, for example as 85% strength phosphoric acid or 37% strength hydrochloric acid. For economic reasons, it is preferable to use the commercially available acid concentration.

The ratio of the Brønstedt acid used to the amine of the formula (III) may vary. Preferably, the ratio of Brønstedt acid to the amine of the formula (III) is in the range of about 5:0.8 to about 1:1.5, in particular of about 3:0.9 to about 1:1.2, specially of about 1.5:1 to about 1:1.1.

The process according to the invention can be carried out in general in vacuo, at atmospheric pressure or under superatmospheric pressure.

The temperatures used may vary depending on the starting materials used. The reaction according to the invention or the process can be carried out at temperatures in the range of about 20° C. to about 200° C., preferably at temperatures in the range of about 20° C. to about 150° C.

The stoichiometry of the compounds of the formulae (II) and (III) which are used may vary within wide ranges. The molar ratio of the compound of the formula (II) to the amine of the formula (III) which is used may be about 1:0.5 to about 1:10, in particular about 1:1 to about 1:6, specially about 1:1.05 to about 1:2. The use of larger amounts of compound of the formula (III) is possible in principle but is disadvantageous for economic reasons.

If the reaction is carried out in a solvent, the solvent can be removed after the end of the reaction by distillation. This can be effected under atmospheric pressure or reduced pressure at room temperature or elevated temperatures.

After the end of the reaction, the resulting ammonium salts can be removed by extraction with water. The isolation of the desired compounds of the formula (I) can be effected by customary methods.

4-(methylamino)furan-2(5H)-one derivatives of the formula (II) are known in some cases and/or can be prepared by customary methods.

The preparation of compound of the formula (II) in which $R^2$ represents methyl is described, for example, in Heterocycles Vol. 27, 8, 1988, 1907-1923. The preparation of compounds of the formula (II) in which $R^2$ represents hydrogen is described, for example, in WO 2009/036898.

One synthesis route for compounds of the formula (II), in which $R^2$ represents H or alkyl according to the invention, is shown in Scheme 3. Starting from 4-chloroacetoacetate (4), a compound of the formula (II) in which $R^2$ represents H is prepared and is then reacted with an alkylating agent X—$R^{2'}$. $R^{2'}$ here represents an alkyl group according to the invention and X represents a suitable leaving group. Suitable leaving groups are those which have sufficient nucleofugicity under the prevailing reaction conditions, such as, for example, halogens (e.g. Cl, Br, or iodine), mesylate, tosylate or $SO_2Me$, in particular Cl, Br and mesylate.

Scheme 3:

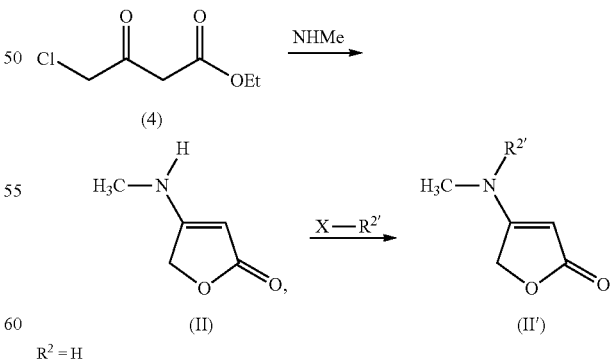

In the context of the present invention, the term "alkyl", either alone or in combination with further terms, for example, haloalkyl, alkoxyalkyl, cycloalkylalkyl, halocycloalkylalkyl and arylalkyl, is understood as meaning a radical of a saturated, aliphatic hydrocarbon group having 1 to 12 carbon atoms, which may be branched or straight-chain. Examples of $C_{1-12}$-alkyl radicals are methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1-ethylpropyl, 1,2-dimethylpropyl, hexyl, n-heptyl, n-octyl, n-nonyl, n-decyl, n-undecyl and n-dodecyl. Among these alkyl radicals, $C_{1-6}$-alkyl radicals are particularly preferred. $C_{1-4}$-alkyl radicals are particularly preferred, specially methyl and ethyl.

The term "alkenyl" is understood as meaning, according to the invention, a linear or branched $C_{2-12}$-alkenyl radical which has at least one double bond, for example vinyl, allyl, 1-propenyl, isopropenyl, 1-butenyl, 2-butenyl, 3-butenyl, 1,3-butanedienyl, 1-pentenyl, 2-pentenyl, 3-pentenyl, 4-pentenyl, 1,3-pentanedienyl, 1-hexenyl, 2-hexenyl, 3-hexenyl, 4-hexenyl, 5-hexenyl and 1,4-hexanedienyl. Preferred among these are $C_{2-6}$-alkenyl radicals, and $C_{2-4}$-alkenyl radicals are particularly preferred.

The term "alkynyl" is understood as meaning, according to the invention, a linear or branched $C_{2-12}$-alkynyl radical which has at least one triple bond, for example ethynyl, 1-propynyl and propargyl. Preferred among these are $C_{2-6}$-alkynyl radicals, and $C_{3-4}$-alkynyl radicals are particularly preferred. The alkynyl radical may also have at least one double bond.

The term "cycloalkyl" is understood as meaning, according to the invention, a $C_{3-8}$-cycloalkyl radical, for example cyclopropyl, cyclobutyl, cyclopentyl, cyclohexyl, cycloheptyl and cyclooctyl, Preferred among these are $C_{3-6}$-cycloalkyl radicals.

The term "aryl" is understood as meaning, according to the invention, an aromatic ring having 6 to 14 carbon atoms, preferably phenyl.

The term "arylalkyl" is understood as meaning a combination of "aryl" and "alkyl" radicals defined according to the invention, the radical generally being bonded by the alkyl group. Examples of these are benzyl, phenylethyl or α-methylbenzyl, benzyl being particularly preferred.

In the context of the present invention, radicals substituted by halogen, for example haloalkyl, are understood as meaning radicals mono- or polyhalogenated up to the maximum possible number of substituents. In the case of polyhalogenation, the halogen atoms can be identical or different. Halogen represents fluorine, chlorine, bromine or iodine, in particular fluorine, chlorine or bromine.

The term "alkoxy", either alone or in combination with further terms, for example, haloalkoxy, is understood here as meaning an O-alkyl radical, the term "alkyl" having the abovementioned meaning.

Optionally substituted radicals may be mono- or polysubstituted, with it being possible for the substituents to be identical or different in the case of polysubstitution.

The present invention is explained in more detail with reference to the following examples, without limiting the invention to said examples.

PREPARATION EXAMPLES

Preparation of 4-(dimethylamino)furan-2(5H)-one 2 g (0.18 mol) of 4-(methylamino)furan-2(5H)-one are introduced in 20 ml of 1,2-dimethoxyethane, and 0.72 g of sodium hydroxide is added. 2.2 g of dimethyl sulphate in 5 ml of 1,2-dimethoxyethane are metered into the suspension and stirred at 40° C. for 5 h. The solvent is removed in vacuo and 50 ml of water are added to the residue. This mixture is then extracted with 50 ml of dichloromethane. The organic phase is dried over sodium sulphate and then evaporated down in vacuo. 1.2 g of 4-(dimethylamino)furan-2(5H)-one are obtained as a solid with a purity of 96% (yield 51%).

Example 1

3.9 g of potassium hydrogen sulphate are added at room temperature to a suspension of 4.1 g of 4-(dimethylamino)furan-2(5H)-one and 5 g of N-[(6-chloropyridin-3-yl)methyl]-2,2-difluoroethylamine in 50 ml of butyronitrile. The mixture is refluxed for 8 h. Thereafter, cooling at room temperature and washing twice with 50 ml of water are effected. The solvent is removed in vacuo. 6 g of 4-[[(6-chloropyridin-3-yl)methyl](2,2-difluoroethyl)amino]furan-2(5H)-one are obtained with a purity of 92% (82% yield).

The invention claimed is:

1. A process for preparation of a 4-aminobut-2-enolide of formula (I)

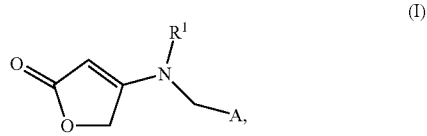

(I)

comprising reacting a 4-(methylamino)furan-2(5H)-one of formula (II)

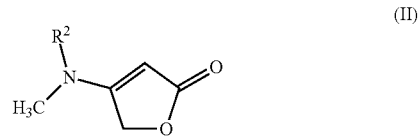

(II)

with an amine of formula (III)

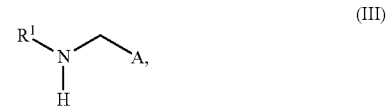

(III)

optionally in the presence of a Brønstedt acid to form a compound of the formula (I), wherein:
$R^1$ represents hydrogen, $C_{1-12}$-alkyl, $C_{1-12}$-haloalkyl, $C_{2-12}$-alkenyl, $C_{2-12}$-haloalkenyl, $C_{2-6}$-alkynyl, $C_{3-8}$-cycloalkyl, $C_{3-8}$-cycloalkyl-$C_{1-6}$-alkyl, $C_{3-8}$-halocycloalkyl, $C_{1-12}$-alkoxy, $C_{1-6}$-alkoxy-$C_{1-6}$-alkyl, $C_{3-8}$-halocycloalkyl-$C_{1-6}$-alkyl or aryl-$C_{1-6}$-alkyl;
$R^2$ represents $C_{1-12}$-alkyl, aryl or aryl-$C_{1-6}$-alkyl; and
A represents pyrid-2-yl, pyrid-4-yl or pyrid-3-yl, which is optionally substituted in the 6-position by F, Cl, Br, $CH_3$, $CF_3$, or $OCF_3$, or represents pyridazin-3-yl which is optionally substituted in the 6-position by Cl or $CH_3$, or represents pyrazin-3-yl, or 2-chloropyrazin-5-yl, or represents 1,3-thiazol-5-yl optionally substituted in the 2-position by Cl or $CH_3$, or represents pyrimidinyl, pyrazolyl, thiophenyl, oxazolyl, isoxazolyl, 1,2,4-oxadiazolyl, isothiazolyl, 1,2,4-triazolyl or 1,2,5-thiadiazolyl, which is optionally substituted by F, Cl, Br, CN, $NO_2$, $C_{1-4}$-alkyl, $C_{1-3}$-alkylthio or $C_{1-3}$-alkylsulphonyl, where each of the radicals $C_{1-4}$-alkyl, $C_{1-3}$-alkylthio and $C_{1-3}$-alkylsulphonyl may be substituted by F, chlorine, or a combination thereof or represents a substituted heterocyclyl of the following formula

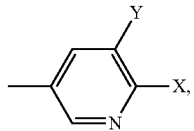

in which:

X represents halogen, $C_{1-12}$-alkyl or $C_{1-12}$-haloalkyl, and

Y represents halogen, $C_{1-12}$-alkyl, $C_{1-12}$-haloalkyl, $C_{1-12}$-haloalkoxy, azido or CN.

2. The process according to claim 1, wherein, in compound (III), $R^1$ represents $C_{1-6}$-alkyl, $C_{1-6}$-haloalkyl, $C_{2-6}$-alkenyl, $C_{2-6}$-haloalkenyl, $C_{2-6}$-alkynyl, $C_{3-8}$-cycloalkyl, $C_{3-8}$-cycloalkyl-$C_{1-6}$-alkyl, $C_{3-8}$-halocycloalkyl, $C_{3-8}$-halocycloalkyl-$C_{1-6}$-alkyl or $C_{1-6}$-alkoxy-$C_{1-6}$-alkyl; and A is selected from 6-fluoropyrid-3-yl, 6-chloropyrid-3-yl, 6-bromopyrid-3-yl, 6-methylpyrid-3-yl, 6-trifluoromethylpyrid-3-yl, 6-trifluoromethoxypyrid-3-yl, 6-chloro-1,4-pyridazin-3-yl, 6-methyl-1,4-pyridazin-3-yl, 2-chloro-1,3-thiazol-5-yl or 2-methyl-1,3-thiazol-5-yl, 2-chloropyrimidin-5-yl, 2-trifluoromethylpyrimidin-5-yl, 5,6-difluoropyrid-3-yl, 5-chloro-6-fluoropyrid-3-yl, 5-bromo-6-fluoropyrid-3-yl, 5-iodo-6-fluoropyrid-3-yl, 5-fluoro-6-chloropyrid-3-yl, 5,6-dichloropyrid-3-yl, 5-bromo-6-chloropyrid-3-yl, 5-iodo-6-chloropyrid-3-yl, 5-fluoro-6-bromopyrid-3-yl, 5-chloro-6-bromopyrid-3-yl, 5,6-dibromopyrid-3-yl, 5-fluoro-6-iodopyrid-3-yl, 5-chloro-6-iodopyrid-3-yl, 5-bromo-6-iodopyrid-3-yl, 5-methyl-6-fluoropyrid-3-yl, 5-methyl-6-chloropyrid-3-yl, 5-methyl-6-bromopyrid-3-yl, 5-methyl-6-iodopyrid-3-yl, 5-difluoromethyl-6-fluoropyrid-3-yl, 5-difluoromethyl-6-chloropyrid-3-yl, 5-difluoromethyl-6-bromopyrid-3-yl or 5-difluoromethyl-6-iodopyrid-3-yl.

3. The process according to claim 1, wherein said reacting occurs in the presence of a Brønstedt acid selected from the group consisting of phosphoric acid, sulphuric acid, hydrochloric acid, hydrobromic acid, hydrofluoric acid, potassium hydrogen sulphate, trifluoroacetic acid, acetic acid, methanesulphonic acid and p-toluenesulphonic acid.

4. The process according to claim 1, wherein the compound of formula (II) and the amine of formula (III) are provided in a molar ratio of 1:0.5 to 1:10.

5. The process according to claim 1, wherein the ratio of the Brønstedt acid used to the amine of formula (III) is in a range of about 5:0.8 to about 1:1.5.

6. The process according to claim 2, wherein said reacting occurs in the presence of a Brønstedt acid selected from the group consisting of phosphoric acid, sulphuric acid, hydrochloric acid, hydrobromic acid, hydrofluoric acid, potassium hydrogen sulphate, trifluoroacetic acid, acetic acid, methanesulphonic acid and p-toluenesulphonic acid.

7. The process according to claim 2, wherein the compound of formula (II) and the amine of formula (III) are provided in a molar ratio of 1:0.5 to 1:10.

8. The process according to claim 2, wherein the ratio of the Brønstedt acid used to the amine of formula (III) is in a range of about 5:0.8 to about 1:1.5.

9. The process according to claim 3, wherein the compound of formula (II) and the amine of formula (III) are provided in a molar ratio of 1:0.5 to 1:10.

10. The process according to claim 3, wherein the ratio of the Brønstedt acid used to the amine of formula (III) is in a range of about 5:0.8 to about 1:1.5.

11. The process according to claim 4, wherein the ratio of the Brønstedt acid used to the amine of formula (III) is in a range of about 5:0.8 to about 1:1.5.

* * * * *